US 6,569,189 B1

(12) United States Patent
Augustine et al.

(10) Patent No.: US 6,569,189 B1
(45) Date of Patent: May 27, 2003

(54) TISSUE TREATMENT APPARATUS INCLUDING A BANDPASS FILTER TRANSPARENT TO SELECTED WAVELENGTHS OF IR ELECTROMAGNETIC SPECTRUM

(75) Inventors: Scott D. Augustine, Bloomington, MN (US); John P. Rock, Minneapolis, MN (US); Albert P. Van Duren, Chaska, MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/712,025

(22) Filed: Nov. 14, 2000

Related U.S. Application Data

(63) Continuation-in-part of application No. 09/056,063, filed on Apr. 6, 1998, now Pat. No. 6,080,189.

(51) Int. Cl.$^7$ ................................................. A61F 7/00
(52) U.S. Cl. ..................... 607/96; 607/108; 607/114; 602/2; 602/14; 602/41; 602/42
(58) Field of Search .................... 602/1–79; 607/88–91, 607/108–112, 114

(56) References Cited

U.S. PATENT DOCUMENTS

| | | | |
|---|---|---|---|
| 4,979,706 A | * 12/1990 | Aki et al. ................ | 607/88 |
| 5,413,587 A | 5/1995 | Hochstein | |
| 5,431,622 A | 7/1995 | Pyrozyk et al. | |
| 5,662,624 A | 9/1997 | Sundström et al. | |
| 5,702,375 A | 12/1997 | Angelillo et al. | |
| 5,737,774 A | * 4/1998 | Petty-Saphon ............ | 602/2 |
| 6,045,518 A | 4/2000 | Augustine | |
| 6,290,713 B1 | * 9/2001 | Russell ................... | 607/88 |

FOREIGN PATENT DOCUMENTS

WO 64/00090 1/1994

OTHER PUBLICATIONS http://www.barr–associates–uk.com/mm–home.htm, 1 pg.
http://www.barr–associates–uk.com/mms–medical.htm, Medical Applications, 1 p.
http://www.andcorp.com/Web_store/Heat_Filters/ir_suppression.html, Infrared Suppression Filters from Andover Corporation, 2 pgs.
http://www.andcorp.com/Web_store/Heat_Filters/cold_mirror.html, Cold Mirrors from Andover Corporation, 2 pgs.
http://www.andcorp.com/Web_store/heat_Filters/uv_cold mirror.html, Ultraviolet Cold Mirrors from Andover Corporation, 2 pgs.
http://www.andcorp.com/Web_store/Custom_BP/Custom_Filter.html, Custom Bandpass Filters, 2 pgs.

* cited by examiner

Primary Examiner—Robert L. Nassar
(74) Attorney, Agent, or Firm—Gray Cary Ware & Freidenrich; Terrance A. Meador (57) ABSTRACT

A tissue treatment apparatus includes a bandage that is transparent to, or transmissive of, energy in a predetermined range of the infrared (IR) portion of the electromagnetic spectrum. The bandage includes a layer that acts as a bandpass filter, permitting IR radiation in the range of wavelengths between 3 and 30 μm to pass through the bandage to tissue against which the bandage is disposed. A heater is used to generate heat, including IR radiation, and an attachment device retains the heater over or on the bandpass bandage layer. The bandage and heater together have a low profile so as to be convenient for a patient, and are flexible so as to conform to the shape of a wound and to contours of the skin near the wound. The bandage is provided with an adhesive pattern for maintaining moisture at the wound site. The heater may maintain a normothermic condition at subdermal regions of the wound treatment area. A controller may be provided for cycling the temperature of the heater in order to maintain the normothermic condition.

33 Claims, 12 Drawing Sheets

TISSUE TREATMENT APPARATUS INCLUDING A BANDPASS FILTER TRANSPARENT TO SELECTED WAVELENGTHS OF IR ELECTROMAGNETIC SPECTRUM

CROSS-REFERENCES TO RELATED PATENT AND COPENDING APPLICATIONS

This application is a continuation-in-part of U.S. patent application Ser. No. 09/056,063 filed Apr. 6, 1998 now U.S. Pat. No. 6,080,189, entitled "WOUND TREATMENT APPARATUS INCLUDING A HEATER AND IR-TRANSPARENT OR IR-TRANSMISSIVE BANDAGE, and contains subject matter related to the following commonly assigned pending U.S. Patent Applications:

Ser. No. 08/843,072 filed on Apr. 11, 1997, for "FLEXIBLE NON-CONTACT WOUND TREATMENT DEVICE WITH A SINGLE JOINT";

Ser. No. 07/900,656, filed Jun. 19, 1992, for "THERMAL BODY TREATMENT APPARATUS AND METHOD";

Ser. No. 08/342,741, filed Nov. 21, 1994, for WOUND TREATMENT DEVICE";

Ser. No. 08/356,325, filed Feb. 21, 1995, for "WOUND COVERING";

Ser. No. 08/785,794, filed Jan. 21, 1997, for "NORMOTHERMIC HEATER WOUND COVERING";

Ser. No. 08/786,713, filed Jan. 21, 1997, for "NORMOTHERMIC TISSUE HEATING WOUND COVERING";

Ser. No. 08/786,714, filed Jan. 21, 1997, for "NEAR HYPOTHERMIC HEATER WOUND COVERING"; and Ser. No. 08/838,618, filed Apr. 11, 1997, for "FLEXIBLE NON-CONTACT WOUND TREATMENT DEVICE."

This application also contains material related to the following commonly assigned U.S. Patent Applications, which were concurrently filed with this application:

Ser. No. 09/056,191, filed Apr. 6, 1998 for "WOUND TREATMENT APPARATUS WITH A HEAT CONDUCTIVE BANDAGE, AND HEAT-SPREADING MEANS ACTING BETWEEN THE HEATER AND BANDAGE";

Ser. No. 09/055,725, filed Apr. 6, 1998, for "WOUND TREATMENT APPARATUS WITH INFRARED ABSORPTIVE WOUND COVER";

Ser. No. 09/055,597, filed Apr. 6, 1998, for "WOUND TREATMENT APPARATUS WITH A HEATER ADHESIVELY JOINED TO A BANDAGE"; and Ser. No. 09/055,605, filed Apr. 6, 1998, for "WOUND TREATMENT APPARATUS FOR NORMOTHERMIC TREATMENT OF WOUNDS."

BACKGROUND OF THE INVENTION

1. Field of the Invention

The present invention relates to a tissue treatment device with a bandage that is essentially transparent to a predetermined range of wavelengths in the infrared (IR) range of the electromagnetic spectrum, and to a heater that emits energy primarily in the IR range. The bandage and heater are connected or joined by an attachment means that holds the heater in position on or over the bandage.

2. Description of the Related Art

Heat therapy has been used to treat tissue since the days of Hippocrates, with varying results. For example, heat therapy for wounds has involved the application of heat under conditions that make the tissues of a wound hyperthermic. However, hyperthermia impedes wound healing and may actually damage the wound tissues.

The "normal" range of temperature for the human body is 37° C.+1 C. (36° C. to 38° C.). This is termed the "normothermic" range. Humans exhibit a thermoregulatory response to core temperature changes as little as ±1° C., wherein "core" as used herein refers to interior portions of the body. This extremely tight temperature control is necessary because virtually all human cellular functions, chemical reactions and enzymatic reactions are optimum at 37° C. It should be understood that these are human temperature ranges and that different "normothermic" ranges exist for different animal types, resulting in a different target temperature range.

Surface tissue varies in temperature according to where on the body it is located. For example, in humans, the skin of the torso is usually hypothermic, while the skin of the legs is always hypothermic. The normal skin temperature of the distal leg is approximately 32° C., which is considered to be "moderately hypothermic." The skin temperature of the distal leg of a patient with vascular insufficiency may be as low as 25° C., which is "severely hypothermic" The hypothermic condition of wounds and ulcers inhibits healing. Severely hypothermic skin or wound tissue is in a state that may be termed "suspended animation." In suspended animation, tissue is living, but cellular functions necessary for cell division and collagen deposition are slowed or even stopped. Further, the immune system is inhibited, allowing wounds to become heavily colonized with bacteria. The local application of heat to hypothermic tissue will cause some degree of vasodilatation, resulting in an increase in local blood flow. Increased blood flow increases the subcutaneous oxygen tension ($PsqO_2$) which, in turn, increases both collagen deposition and immune function.

Many references report that the immune system is inhibited by hypothermia and activated by mild hyperthermia (fever). Persp Biol Med:439–474, Spring 1980, reports that local body temperature is a critical factor determining host susceptibility, the location of lesions and contracting infectious diseases. New Eng J Med 305:808–814, 1981, reports that animals exposed to cold environments are more susceptible to infectious diseases, whereas exposure to high ambient temperatures often produces a beneficial result. Wound Rep Reg 2:48–56, 1994 and Acta Anaesth Scand 38:201–205, 1994, report that infections caused by a standard inoculum of *E. coli* or *S. aureus* were significantly more severe in hypothermic guinea pigs than in normothermic control animals. New Eng J Med 334:1209–1215, 1996, reports that hypothermic colorectal surgical patients had three times more wound infections (19% vs. 6%) than those who were kept normothermic during surgery with a Bair Hugger® patient warming system described in commonly assigned U.S. Pat. Nos. 5,324,320, 5,300,102 and 5,350,417. Further, six weeks of warming therapy with the Bair Hugger® patient warming system has successfully healed chronic progressive ulcers which heretofore have been resistant to standard therapies.

Currently available medical devices that apply heat to wounds include infrared lights, warm water pads, warm water bottles, whirlpools and Sitz baths. All types of lesions, such as surgical, chronic, traumatic, donor sites, infected wounds and burns, have been treated with these warming modalities. Particularly difficult has been the application of heat to open wounds such as ulcers. Treatment of a wound with infrared light requires that the wound be positioned under the light during therapy, necessitating patient immobility. Further, the infrared heat treatment accelerates the drying of the wound, thereby slowing the healing process. Warm water pads and bottles and electrical heating pads are cumbersome, reduce patient mobility, and are usually applied to the extremities and held in place with inconvenient wraps such as straps, hook-and-eye material or tabs. Whirlpools and Sitz baths reduce mobility and limit the duration of warming therapy due to skin maceration by the water. None of these modalities, with the exception of electrical heating pads, is capable of prolonged heat treatment of a wound.

Each of the various kinds of body tissue, such as epidermal, muscle, and fatty tissue, has a different water content. Epidermal tissue contains a relatively large proportion of water and is known to absorb greater amounts of IR energy at wavelengths of less than 3 microns ($\mu$m) due to the water content. Therefore, when an IR radiation apparatus is used to heat a wound area, it is primarily the skin region that is heated. Many chronic wounds, such as pressure wounds, result from bony prominence pressure points in patients who remain immobile for long periods of time. Other subdermal injuries result in occluded blood flow, either venous or arterial, which deprive the wound area of oxygen. Although such wounds may eventually erupt to the skin surface, the primary wound area is beneath the skin. Because IR radiation primarily affects the skin, IR wound treatment has largely been ineffective for subdermal wounds.

SUMMARY OF THE INVENTION

There is a need for an apparatus to treat tissue, especially subdermal tissue with heat for a prolonged period of time, while promoting patient convenience and mobility. For example, such treatment would be used to produce a substantially normothermic condition at a wound. Such an apparatus should selectively transfer heat to the epidermis, passing beneficial (therapeutic) radiation and blocking radiation that is harmful, be convenient to operate without interfering with the patient's movement or comfort, and be capable of maintaining a moist tissue environment. Such an apparatus should be able to heat subdermal tissue areas without burning the overlying epidermal tissue.

Preferably, the placement of the apparatus is confined to a "tissue treatment area". Such an area may include, for example, a wound, or skin adjacent the wound (the periwound), or both. Such a treatment area may be any area of tissue to which heat is applied for any clinical purpose.

The invention is a tissue treatment apparatus that includes a bandage that is transparent or at least transmissive in a predetermined range of wavelengths in the infrared (IR) range of the electromagnetic spectrum. A heater is disposed on or over the bandage. The heater emits a significant amount of its energy in the IR range at a frequency that is dependent on the surface temperature of the heater. An attachment means holds the heater in position over the bandage.

Other objects and advantages of the invention will become apparent upon reading the following description taken together with the accompanying drawings.

DESCRIPTION OF THE PREFERRED EMBODIMENTS

Referring now to the figures, wherein like reference numerals designate like or similar parts throughout the several views there are shown various embodiments of a tissue treatment apparatus in accordance to this invention.

Figure 1:
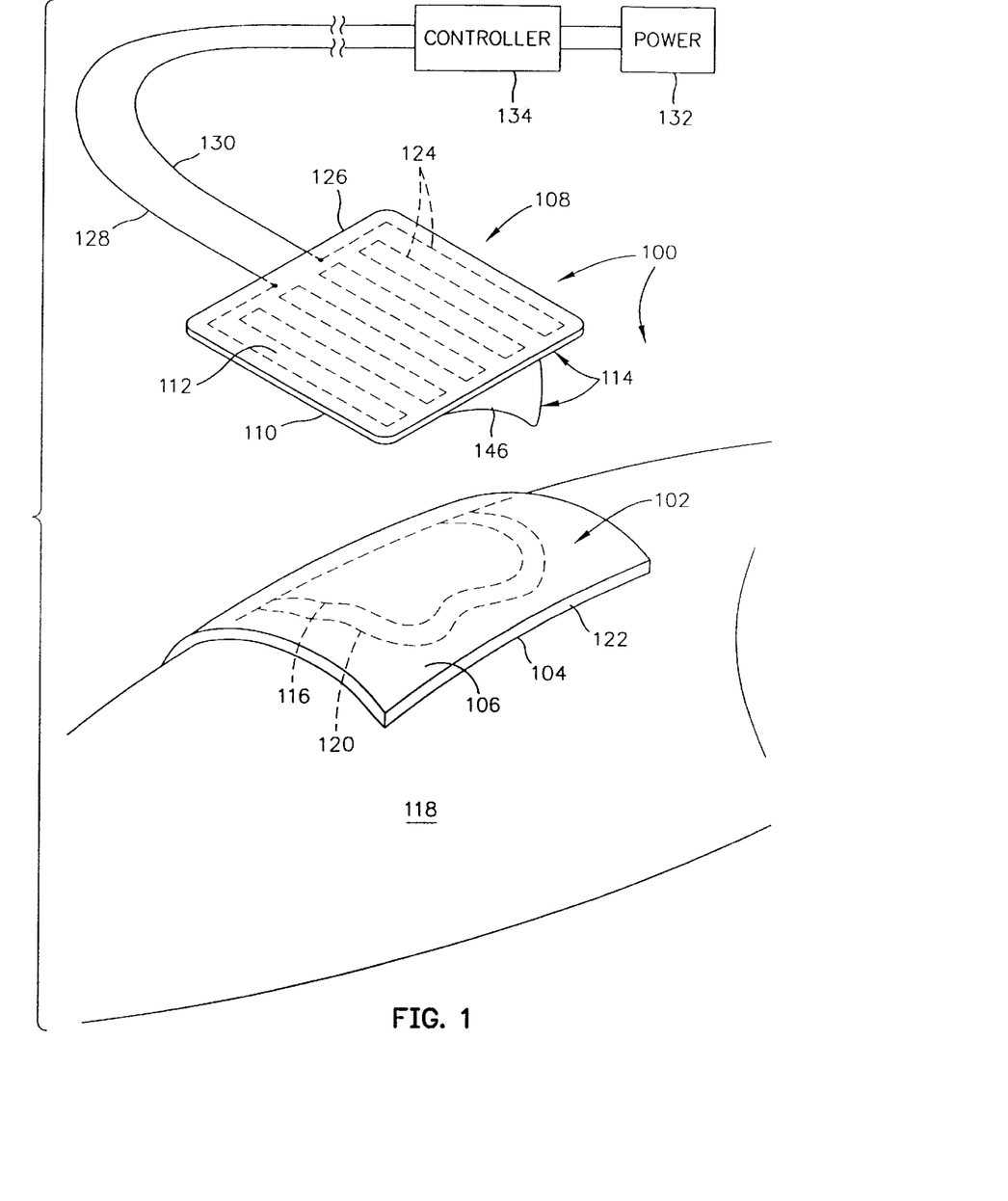
FIG. 1 is an isometric view of a first embodiment of the tissue treatment apparatus being applied to tissue on a person's body where a wound is located.
Figure 2:
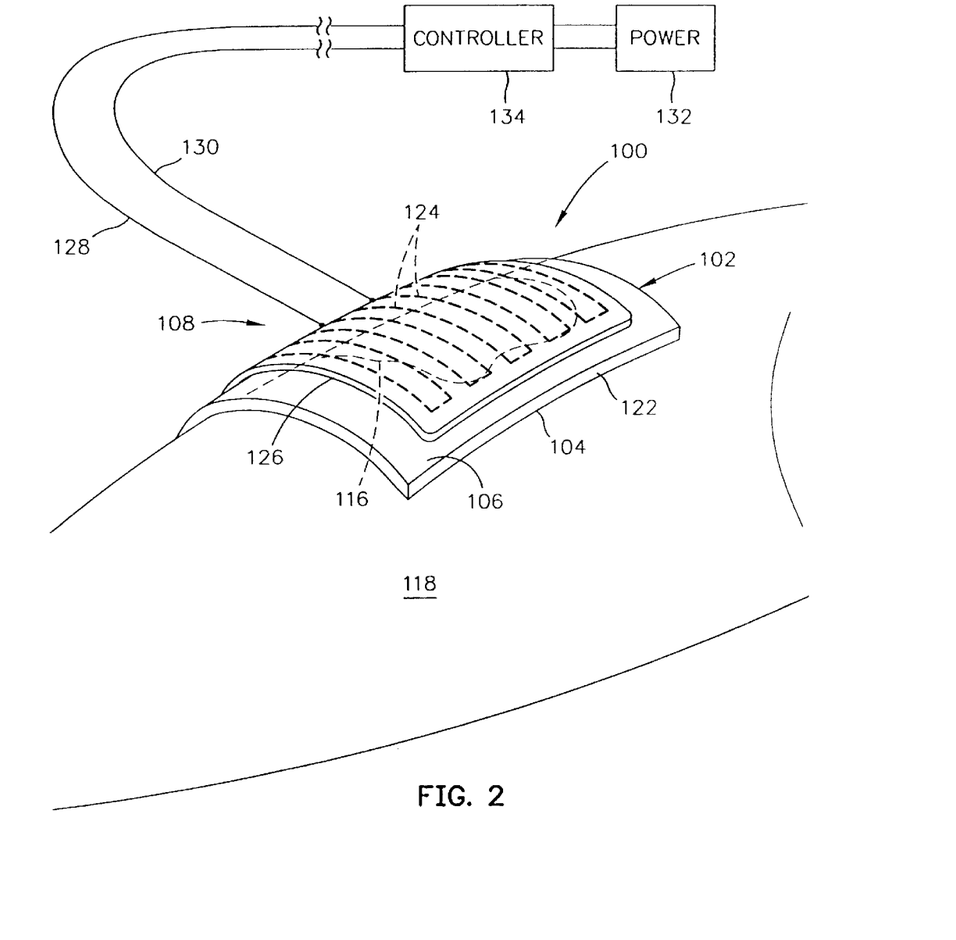
FIG. 2 is an isometric view of the tissue treatment apparatus applied to the person's body.
Figure 3:
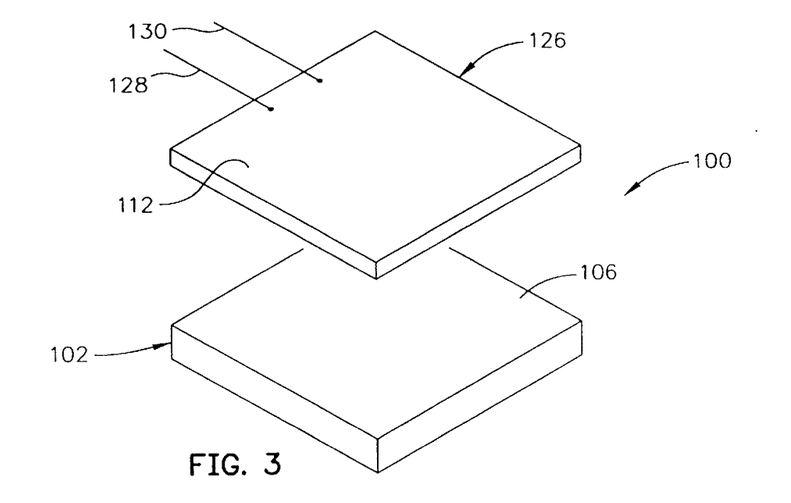
FIG. 3 is an exploded isometric view of the tissue treatment apparatus.
Figure 4:
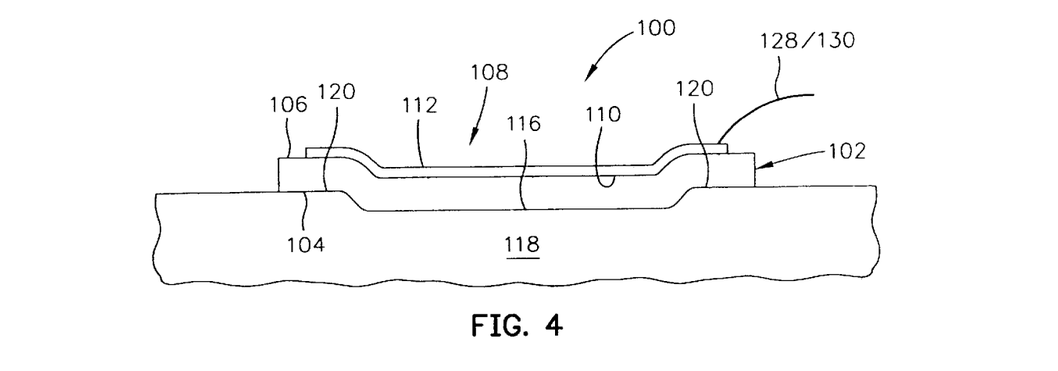
FIG. 4 is a cross-sectional view of the tissue treatment apparatus applied to the person's body.

As shown in FIGS. 1–5, the tissue treatment apparatus 100 includes a bandage 102 fabricated from a material that is transparent to or at least transmissive of energy in the IR range. The bandage 102 has first (lower) and second (upper) surfaces 104 and 106. A heater 108 generates thermal energy and emits a significant amount of this energy in the IR range at a frequency that is dependent on the surface temperature of the heater. This energy passes through the bandage between the first surface 104 and the second surface 106. The heater 108 includes first (lower) and second (upper) surfaces 110 and 112. An attachment means holds the heater 108 in position over the bandage 102 in such a manner as to transfer heat from the heater 108 through the bandage 102 to tissue underneath the bandage. The attachment means may maintain the second surface 106 of the bandage 102 and the first surface 110 of the heater 108 in full, or partial contact, or out of contact. In FIGS. 2 and 4, the tissue treatment apparatus 100 is shown in place to apply heat to tissue beneath the bandage 102. For example, consider tissue that includes a wound 116 of a person's body 118. Immediately adjacent the wound is a periwound area 120, which is typically a peripheral band of tissue around the tissue of the wound area that is less affected by the wound physiology than the wound area tissue.

In the tissue treatment apparatus 100, the heater 108 includes means for generating heat that may be electrically operated. For example, the means may take the form of an electrical resistance element 124 embedded in or laminated to a planar member of flexible material 126, such as polyethylene, silicon, rubber or flexible cloth. In this regard, the heater 108 would form a high emissivity surface or "blackbody" that radiates heat in the form of energy in the IR range. In the preferred embodiment, the heater 108 is substantially planar, as shown in FIGS. 1 and 3, and yet flexible in order that it might conform, with the bandage 102, as shown in FIG. 4, and as shown in FIGS. 2 and 4.

As illustrated in FIGS. 1 and 2, the electrical resistance element 124 is connected to first and second electrical conductors 128 and 130, which are connected to an electrical power source 132, via a controller 134. The purpose of the controller 134 is to control electrical power provided to the electrical resistance element 124. In this regard, the operation of the heater 108 may be cycled or throttled by the controller to maintain the tissue in the treatment area at a normothermic or a near normothermic temperature. As shown in FIGS. 1 and 2, the electrical resistance element 124 may extend back and forth in the flexible planar member 126 with a desired spacing to promote uniform heating of the heater 108.

Figure 5:
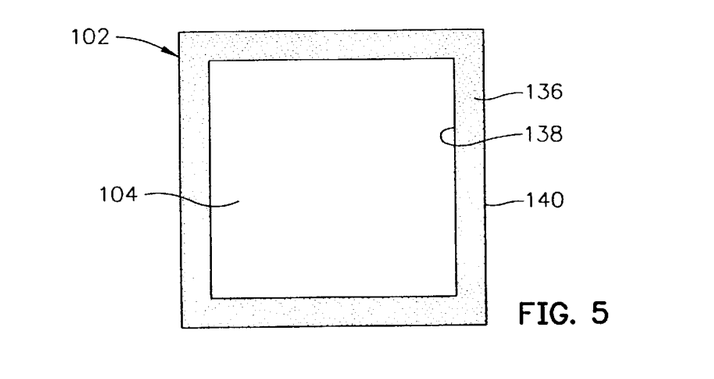
FIG. 5 is a plan view of a second surface of a tissue treatment apparatus bandage.

As shown in FIG. 5, the first surface 104 of the bandage 102 is provided with a pattern of adhesive 136 adjacent its periphery. The adhesive pattern 136 may completely encompass the wound and the periwound tissue so as to trap the natural moisture of the body, which in turn maintains a moist environment across the wound treatment area for wound dessication. Accordingly, the pattern of adhesive 136 has inner and outer boundaries 138 and 140 wherein, in the preferred embodiment, the outer boundary 140 coincides with the outer perimeter of the bandage 102. It should be understood that the bandage 102, the heater 108, and the pattern of adhesive 136 may take various shapes, regular and irregular, depending upon various shapes and contours of wound treatment sites.

The bandage 102 is a flexible, planar member that is fabricated from a material that is substantially transparent to or transmissive of energy in the IR range (approximately 0.5 to 1000 µm) that passes through the bandage between the first and second surfaces (104 and 106) for treatment of tissue under the bandage. The bandage 102 is preferably made from a thin, uncoated, transparent polymeric film. For example, the bandage may be about 127 µm, or less, in thickness. Examples of polymeric film material which, when uncoated, are transparent to or transmit in the IR range include, without limitation: polyurethane, polyethylene, polypropylene, and polyvinyl chloride. Preferably, these materials are uniform in thickness so they cause little or no distortion of the infrared radiation thus providing a uniform transfer of energy through the bandage. The bandage 102 is uncoated on either surface 104 and 106, except for the adhesive pattern 136. Relatedly, the adhesive pattern 136 may comprise any shape or pattern that adheres the first surface 104 of the bandage 102 to a patient's skin, maintains a moist environment at the wound treatment area, and leaves a large portion of the first surface 104 unobstructed so that IR energy may pass there through to the wound treatment area. Since human body tissue comprises a large amount of water, the IR energy generated by the heater 108 and transmitted through the bandage 102 will be absorbed by the tissue in and near the wound treatment area, thereby warming the tissue. Manifestly, the structure of the tissue treatment apparatus 100 as thus far described maintains a closed, humid, heated environment at and over a wound treatment area to promote fast healing of wounded tissue.

Figure 6A:
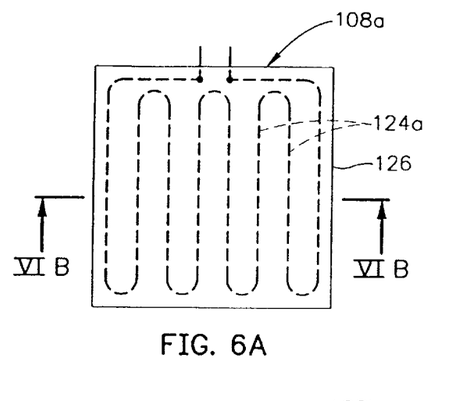
FIG. 6A is a planar illustration of an electrical resistance element embedded in a flexible layer for uniform heating.
Figure 6B:
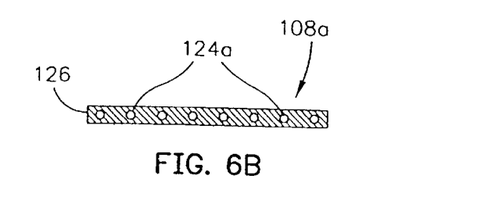
FIG. 6B is a view taken along plane VIB of VIB FIG. 6A.
Figure 7A:
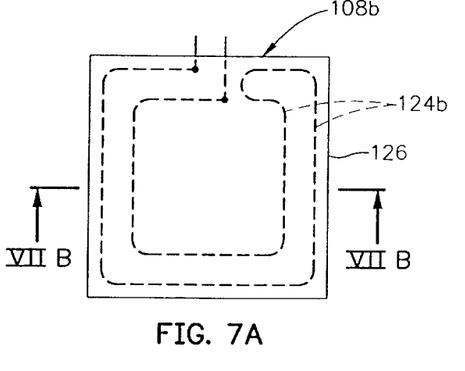
FIG. 7A is a planar view of an electrical resistance element embedded in a flexible layer for heating a portion of a tissue treatment area.
Figure 7B:
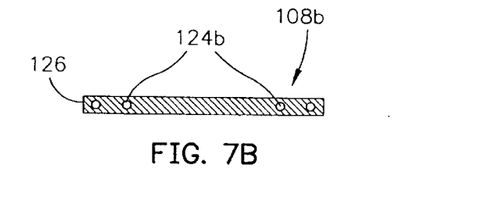
FIG. 7B is a view taken along plane VIIB—VIIB of FIG. 7A.
Figure 8A:
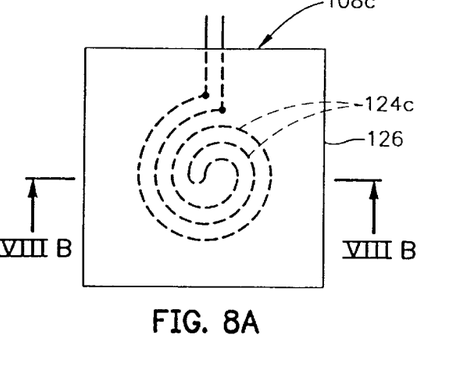
FIG. 8A is a planar view of an electrical resistance element embedded in a flexible layer for uniform heating of a central portion of a tissue treatment area.
Figure 8B:
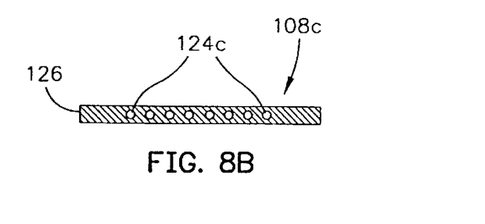
FIG. 8B is a view taken along plane VIIIB—VIIIB of FIG. 8A.

FIGS. 6–8 illustrate various embodiments of electrical resistance elements for the heater 108. In the heater 108a shown in FIG. 6A, an electrical resistance element 124a winds back and forth within the flexible planar member 126, similar to what is shown in FIG. 1. The spacing between the windings of the electrical resistance element 124a may be sized so as to ensure substantially uniform heating of the heater 108a. FIG. 6B shows the electrical resistance element embedded or laminated in the flexible planar member 126. In FIG. 7A, the electrical resistance element 124b takes a path along a peripheral zone of the flexible planar member 126, so that the periphery of the heater 108b is uniformly heated to a temperature greater than a central portion of the heater. Again, these electrical resistance elements 124b are shown embedded or laminated in the flexible planar member 126 in FIG. 7A. In FIG. 8A, the electrical resistance element 124c takes a spiral path out and back within a central region of the heater 108c so as to uniformly heat the central region of the heater to a higher temperature than regions outbound therefrom. The heater 108a is adapted for applying heat to both the wound and periwound area 116 and 120 in FIG. 4, the heater 108b is adapted for applying heat primarily to the periwound area 120 and the heater 108c is adapted for applying heat primarily to the wound 116.

Although the means in the heater 108 for generating heat is disclosed and described above as being electrically-actuated, this is not intended to limit the heater 108 solely to electrical operation. In fact, other heat generating means that would be suitable for the heater 108 include, without limitation, chemical heaters, water pad heaters, and phase-change heaters. Chemical heaters and phase-change heaters would preferably be formed into a relatively thin pad and sealed in a pouch made of polymeric film. A water pad heater can be fabricated by thermo-forming two sheets of polymeric film into fluid channels and sealing the sheets at their peripheries. Warm water is then circulated through the pad from an external source of hot water.

Many surfaces of the body have convexities and concavities in close proximity to one another. See for example the profile of the person's body 118 in the vicinity of the wound 116 in FIG. 4. The bandage 102, in being transparent to or transmissive of energy in the IR region, is important because of the difficulty in achieving a continuous, uniform thermal contact for conductive heat transfer between the upper surface 106 of the bandage 102 and the first surface 110 of the heater 108, even when the heater 108 is fabricated to be moderately flexible and substantially planar. Even a highly flexible planar heater will tend to rest on top of the convexities and not touch the bottom of the concavities. For example, consider the profile of an ulcer on the skin. Consider further that base of the ulcer is sharply recessed. In this case, the base of the ulcer may not even be contacted by the first surface 104 of the bandage 102.

The invention contemplates that the first surface 110 of the heater 108 may be in full, or partial contact with the second surface 106 of the bandage 102. In the areas where the first surface 110 and the second surface 106 are in contact, heat will be transferred by conduction between the first surface 110 and the second surface 106. However, it may be very difficult to conform even the most flexible, substantially planar configuration of the heater 108 to the contours of the human body, and further to the contours of any particular wound. Therefore, in many cases, areas of non-contact between the heater 108 and the second surface 106 will exist, creating air spaces which act as pockets of thermal insulation.

In prior art heater/bandage combinations only inefficient convective heat transfer occurs in air spaces because the bandages are not transparent in the IR (infra red) region. The areas of contact (supporting conductive heat transfer) and the areas of non-contact (supporting convective heat transfer) may have large and unpredictable differences in temperature and heat transfer, resulting in substantial non-uniformities in distribution of the heat across the prior art bandages. The result is that, with prior art heater/bandage combinations, heating of the wound treatment area may be uneven, unpredictable, and ineffective in treating a wound.

With the bandage 102 being fabricated from material that is transparent to or transmissive of energy in the IR range, and with the heater 108 acting as a radiating graybody, a significant component of heat is transferred to, and through, the bandage 102 by radiation. Therefore, in the areas where the first surface 110 of the heater 108 does not contact the second surface 106 of the bandage 102, significant amounts of heat will be transferred by radiation. The invention therefore overcomes the inherent unevenness of heat transfer to the wound treatment area in the prior art heater/bandage combinations where heat transfer from heater to bandage is by conduction and convection only. In this invention, heat transfer between the heater 108 and the bandage 102 is by conduction, convection, and radiation. This provides more efficient, and more uniform, heat transfer from the heater 108 to the bandage 102. This creates a more uniform distribution of heat in, and through, the bandage 102, providing a more even distribution of heat across the tissue in and near the wound treatment area.

This invention further improves on the prior art modes of treating tissue with IR energy as, for example, where wounds are exposed to the output of high temperature heat lamps. In cases such as these, the heat lamps shine on open, exposed wound treatment areas, causing drying of wound tissue, which inhibits and delays healing. This invention interposes an IR transparent (or transmissive) film bandage layer between the IR heat source and the wound which seals about the wound, retaining humidity at the wound and preventing its drying.

Figure 9A:
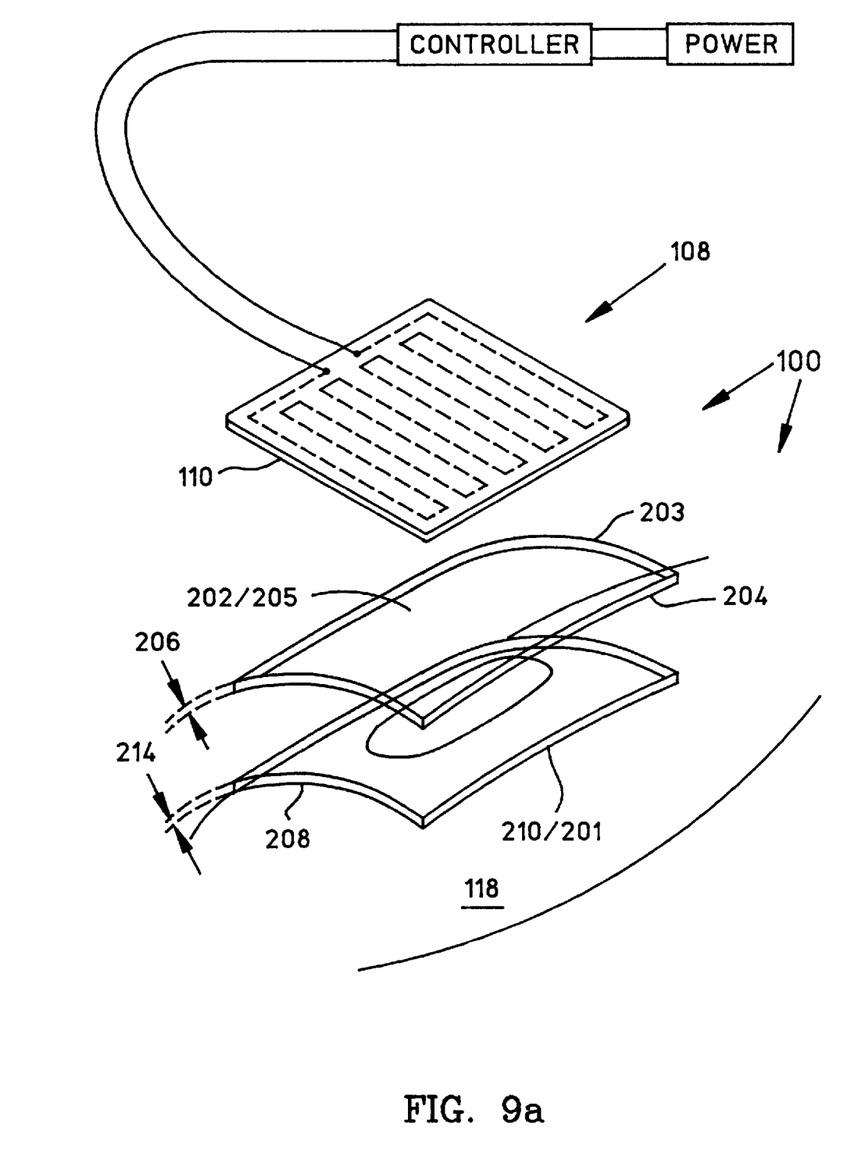
FIGS. 9a and 9b are isometric views of a tissue treatment apparatus embodiment that filters predetermined wavelengths of IR electromagnetic radiation.
Figure 9B:
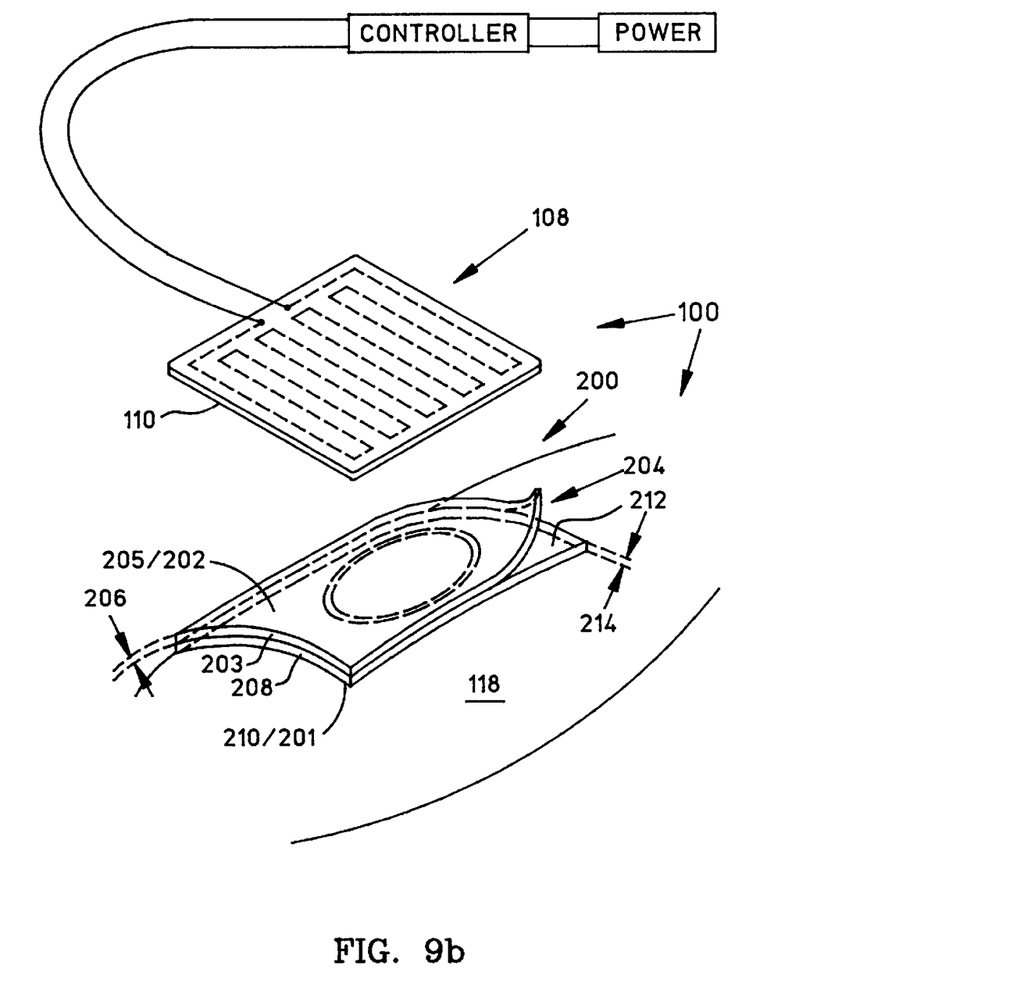

FIGS. 9a and 9b are isometric views of a tissue treatment apparatus that filters predetermined wavelengths of IR electromagnetic radiation. The tissue treatment apparatus 100 includes a bandage 200 having a first surface 201 and a second surface 202. However, the bandage may also include several layers. An IR filter layer of 203 is composed of a flexible planar sheet of material that is transparent to energy in a predetermined first range of wavelengths of IR. In this regard, the IR filter layer acts as anIR bandpass filter. The IR filter layer 203 has a first (lower) surface 204, a second (upper) surface 205, and a thickness 206. In some aspects of the invention, the bandage first surface 201 and the IR filter layer upper surface 205 are the same. As shown, the IR filter layer 203 overlies an IR transparent layer 208 having a first (lower) surface 210. In some aspects of the invention, the bandage first surface 201 and the IR transparent layer first surface 210 are the same. The IR transparent layer 208 has a second (upper) 212 surface adjacent the first surface 204 of the IR filter layer 203. The IR transparent layer 208 has a thickness 214. As described above in the explanation of bandage 102, the IR transparent layer 208 is substantially transparent to IR radiation. Alternately, the attenuation of different wavelengths of IR is uniform through the IR transparent layer 208. Therefore, the combination of the IR transparent layer 208 and the IR filter layer 203 acts to filter the transmission of IR energy passing through the bandage to tissue under the bandage, permitting the transmission of energy in the first range of wavelengths. In some aspects of the invention, the second surface 205 of the IR filter layer 203 is the second bandage surface 202. This second bandage surface 202 interfaces with the first surface 110 of heater 108.

In some aspects of the invention, the IR filter layer 203 acts as a bandpass filter to substantially pass IR wavelengths in the range from 3 to 30 $\mu$m. It is believed that this range of wavelengths is less likely to stress the epidermal tissue as the subdermal tissue of the wound area is being heat treated. Alternately stated, the subdermal tissue is optimally treated by limiting the IR radiation to wavelengths in the range between 3 and 30 $\mu$m. The effectiveness of the IR filter layer 203, as an IR filter which selectively attenuates IR wavelengths, is relative. The actual attenuation or transmissivity of 3 to 30 $\mu$m wavelength IR radiation is dependent on a variety of factors such as the material of bandage layer 203, the thickness, the monomeric orientation, doping agents, and surface coating. It should be understood that the transmissivity or attenuation through the IR transparent layer 208 also varies in response to material type and thickness.

Figure 10A:
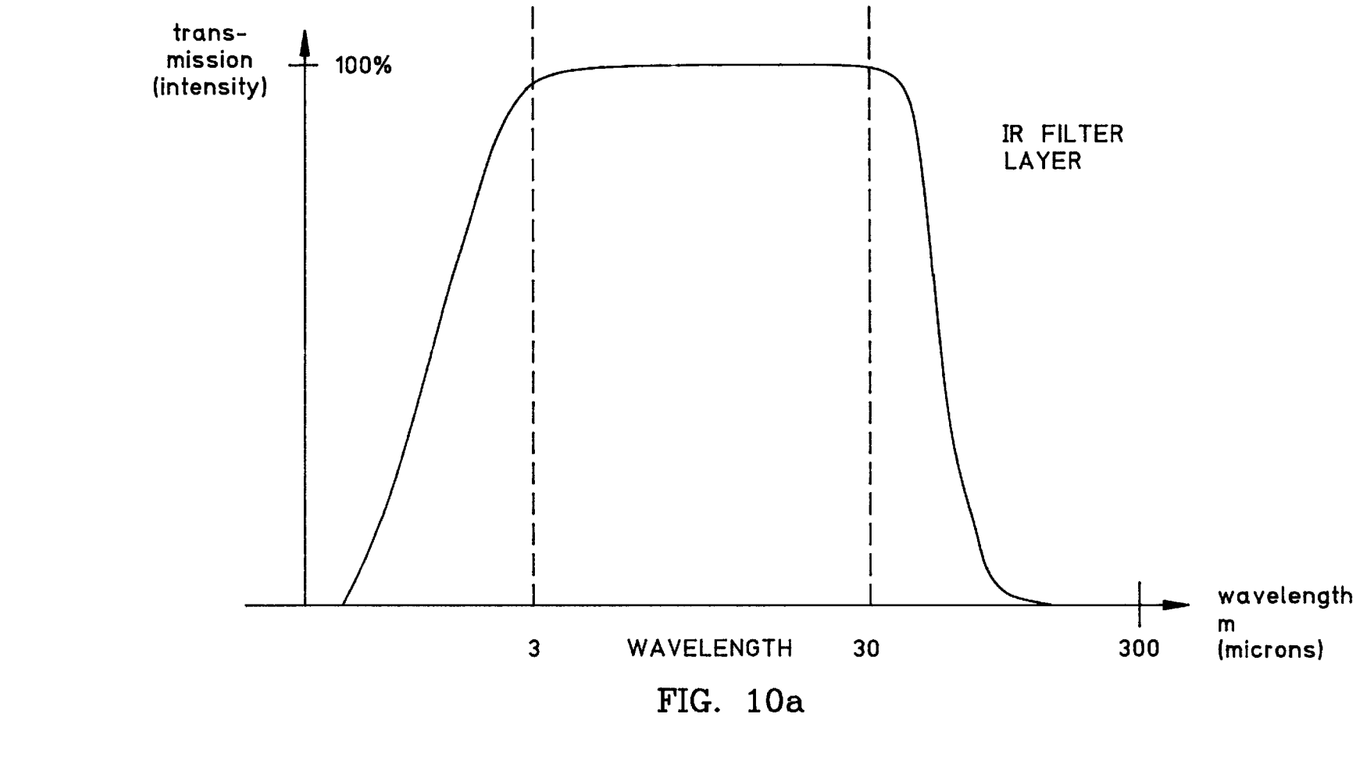
FIGS. 10a–10d illustrate the attenuation characteristics of some exemplary IR filters.

FIGS. 10a–10d illustrate the transmission characteristics of some exemplary IR filters. FIG. 10a is a graph depicting the relationship between IR transmission through the IR bandpass filter layer, and the IR wavelength. As can be seen from the graph, the IR filter layer 203 is substantially transparent in the wavelengths between 3 and 30 $\mu$m. However, the shape of the IR response can be more precisely defined or altered. In some aspects of the invention materials and material thicknesses of IR filter layer 203 are manipulated to shape the bandpass characteristics of the IR filter layer 203. Bandpass characteristics include a definition of the absolute IR transmission intensity (or attenuation) at center wavelength (frequency) and the transmission intensity at center wavelength with respect to off-center wavelengths. The shape of the IR filtration can be defined to include the symmetry of the filtering. In this manner, filter shapes with different attentaution characteristics can be used for different therapies.

Figure 10B:
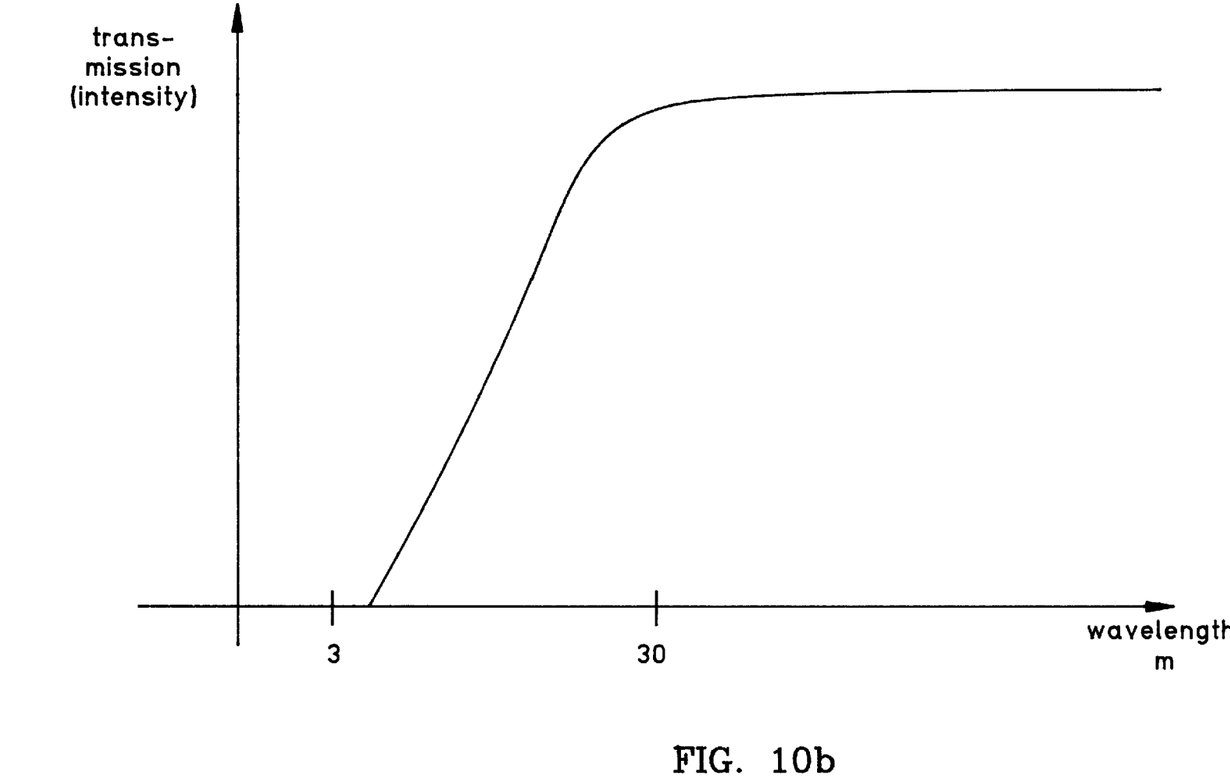

FIG. 10b is a graph illustrating a high pass IR filter layer. In the example given, a asymmetrically shaped IR filter layer may be used when wavelengths above 30 $\mu$m are more preferably transmitted the to wound than IR wavelengths below 3 $\mu$m, as shown. Alternately, a low pass IR filter layer may be shaped to transmit IR wavelengths below 3 $\mu$m, but to attenuate IR wavelengths above 30 $\mu$m (not shown).

Figure 10C:
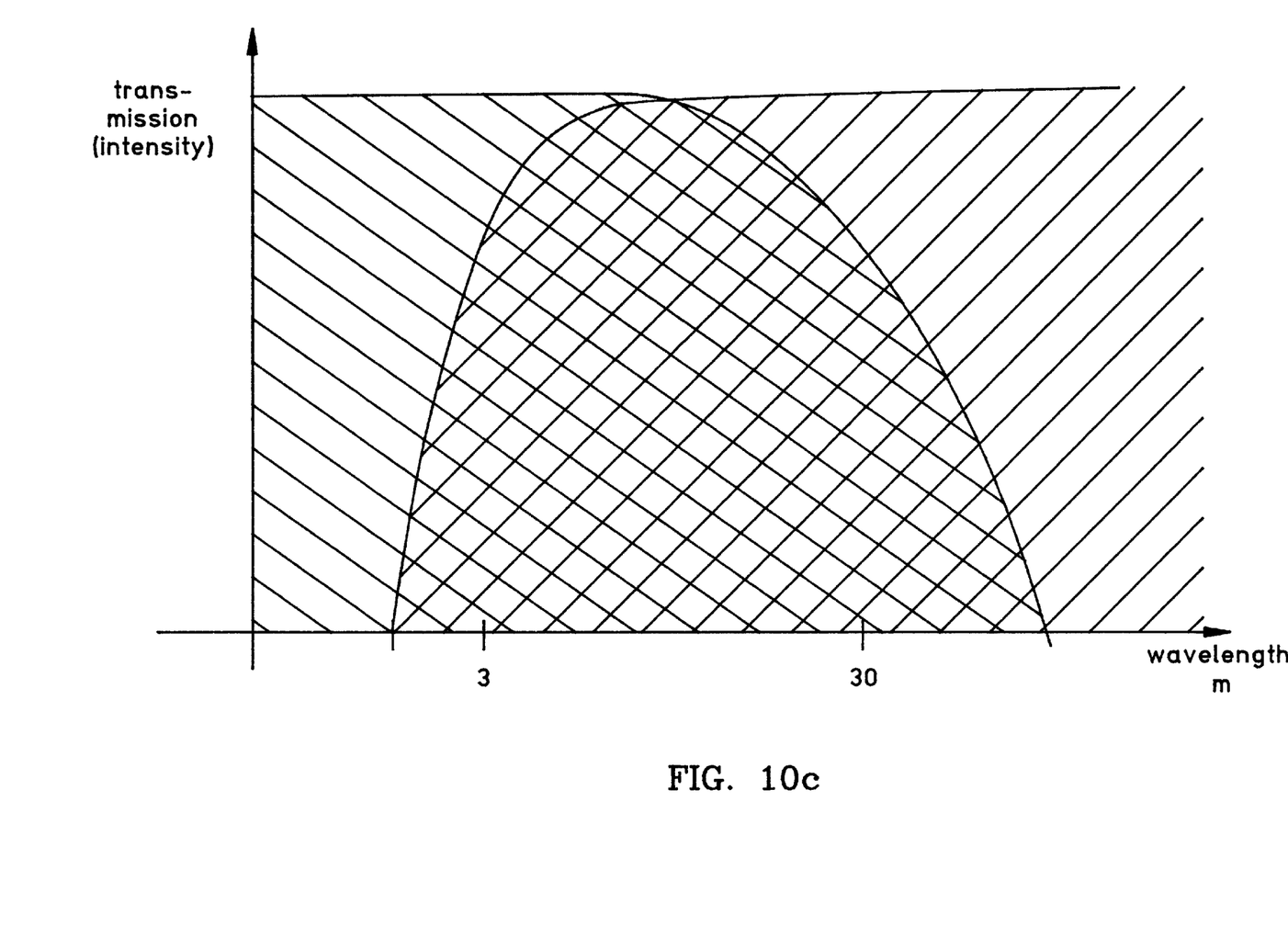

FIG. 10c is a graph illustrating the effect of stacking multiple IR filters. Returning briefly to FIGS. 9a and 9b, although not explicitly shown, in some aspects of the invention the IR filter layer 203 is provided as a stack of IR filter layers. In another alternative, the IR transparent layer 208 is replaced with one or more additional IR filter layers. As shown in FIG. 10c, two IR filters, one strongly attenuating IR wavelengths above 30 $\mu$m (as shown in FIG. 10b), and one strongly attenuating IR wavelengths below 3 $\mu$m can be stacked to form an IR filter that has approximately the response of the IR bandpass filter of FIG. 10a. As shown, the double cross-hatched area of the graph between 3 and 30 $\mu$m illustrates the transmissive properties of the above-described filter of stacked layers.

In other aspects of the invention, the frequencies of the filters can be offset, or the attenuation responses of the IR filer layers can be modified to change the transmission characteristics of the filter. For example, a symmetric filter can be stacked with a filter that provides little attenuation above 30 µm so that wavelengths above 30 µm are not attenuated as much as wavelengths below 3 µm.

Figure 10D:
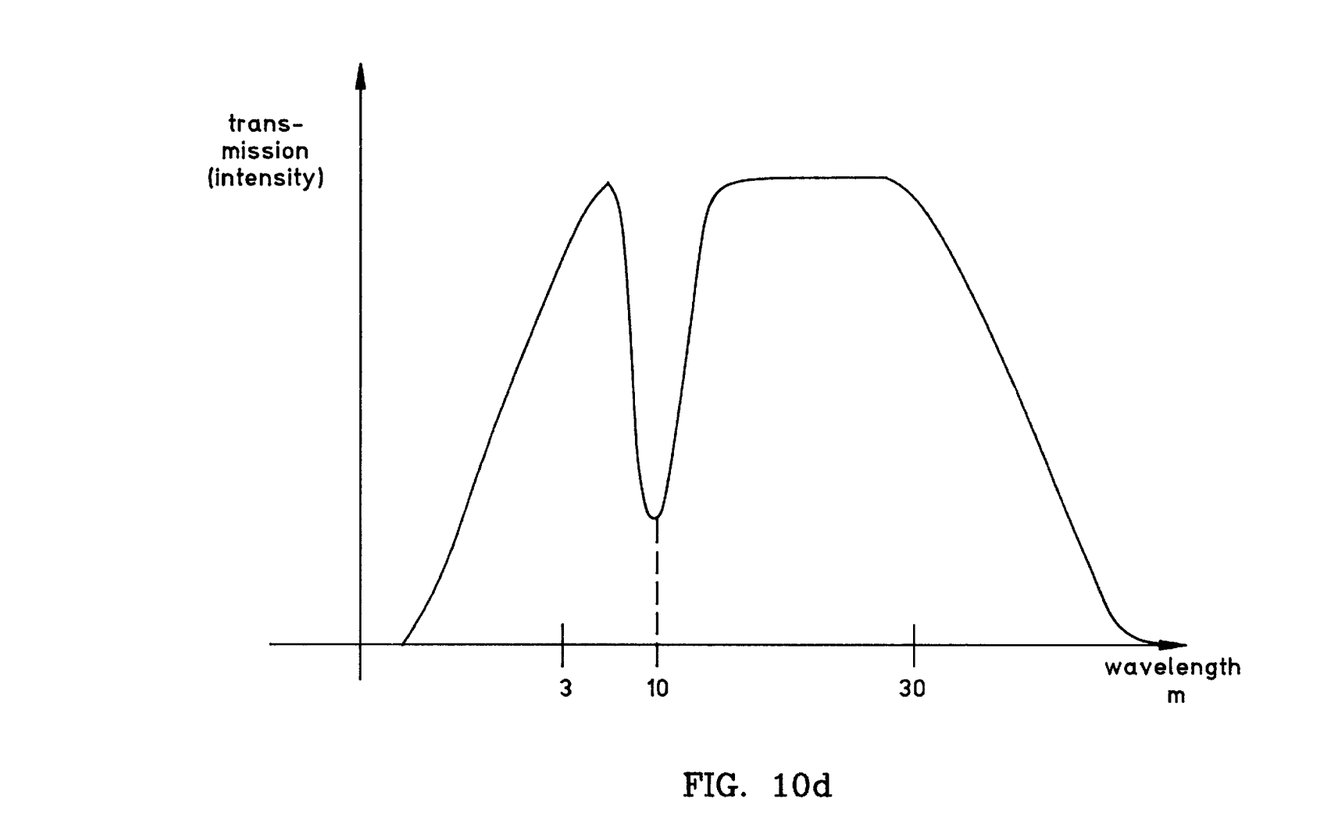

FIG. 10d illustrates an IR bandpass filter with a notch at a wavelength of approximately 10 µm. This notch permits IR wavelengths within a range to be transmitted through the bandage, while excluding a very narrow portion of the passband. Such a filter can be made by combining the IR bandpass filter of FIG. 10a, with an IR filter layer that is transparent to all IR wavelengths, except those wavelengths around 10 µm.

The basic IR filter materials needed to fabricate IR filter layer 203 are available from manufactures such as Andover Corporation (www.andcorp.com), which lists materials with specified wavelength passbands. Custom made filters are also available from such manufacturers.

In the above discussions of the tissue treatment apparatus 100, it has been assumed that the heater 108 emits energy uniformly across the IR electromagnetic spectrum. However, in some aspects of the invention the heater 108 may output different energy levels at different wavelengths. For example, the heater 108 may uniformly emit energy in the predetermined band of IR wavelengths, such as the 3 to 30 µm band. Then, the heater 108 can be used with the IR transparent bandage 102, described in FIGS. 1–5, to achieve the net effect of a bandage that transmits energy in a predetermined band of IR wavelengths. Alternately, the heater 108 may be designed not to emit energy at the off-center wavelengths uniformly, but to transmit more IR energy at either the high or low side from the center wavelength. In other aspects of the invention, the selective IR wavelength transmission characteristics of such a heater 108 can be combined with IR filter layer 203 to accentuate the transmission or attenuation of certain IR wavelength bands.

In some aspects of the invention the emission of IR energy by the heater 208 may include the energy at an IR wavelength that is dependent upon the temperature of heater surface 110. The relationship between surface temperature and IR energy introduces an element of feedback control into the tissue treatment apparatus 100. As tissue underneath the apparatus becomes heated, the heater responds by emitting more energy in a band outside 3 to 30 µm. Then a bandpass IR filter layer 203 is used, the result is the transmission of less IR energy to the underlying tissue, so that the tissue becomes less heated. Likewise, if the tissue becomes too cool, as measured at the heater surface 110, the heater 108 begins to emit more energy in the 3 to 30 µm band of wavelengths. In some aspects of the invention an electrical sensor (not shown) located on or near first surface 110 provides temperature information to controller 134 (see FIG. 9), and the controller 134 provides for selective energy emissions in response to the sensor. The controller makes IR energy emission decisions based upon a stored relationship between heater surface temperature and IR wavelengths likely to produce those temperatures. Alternately, the controller adaptively learns between IR wavelength and temperature as the tissue treatment apparatus is used.

Figure 11:
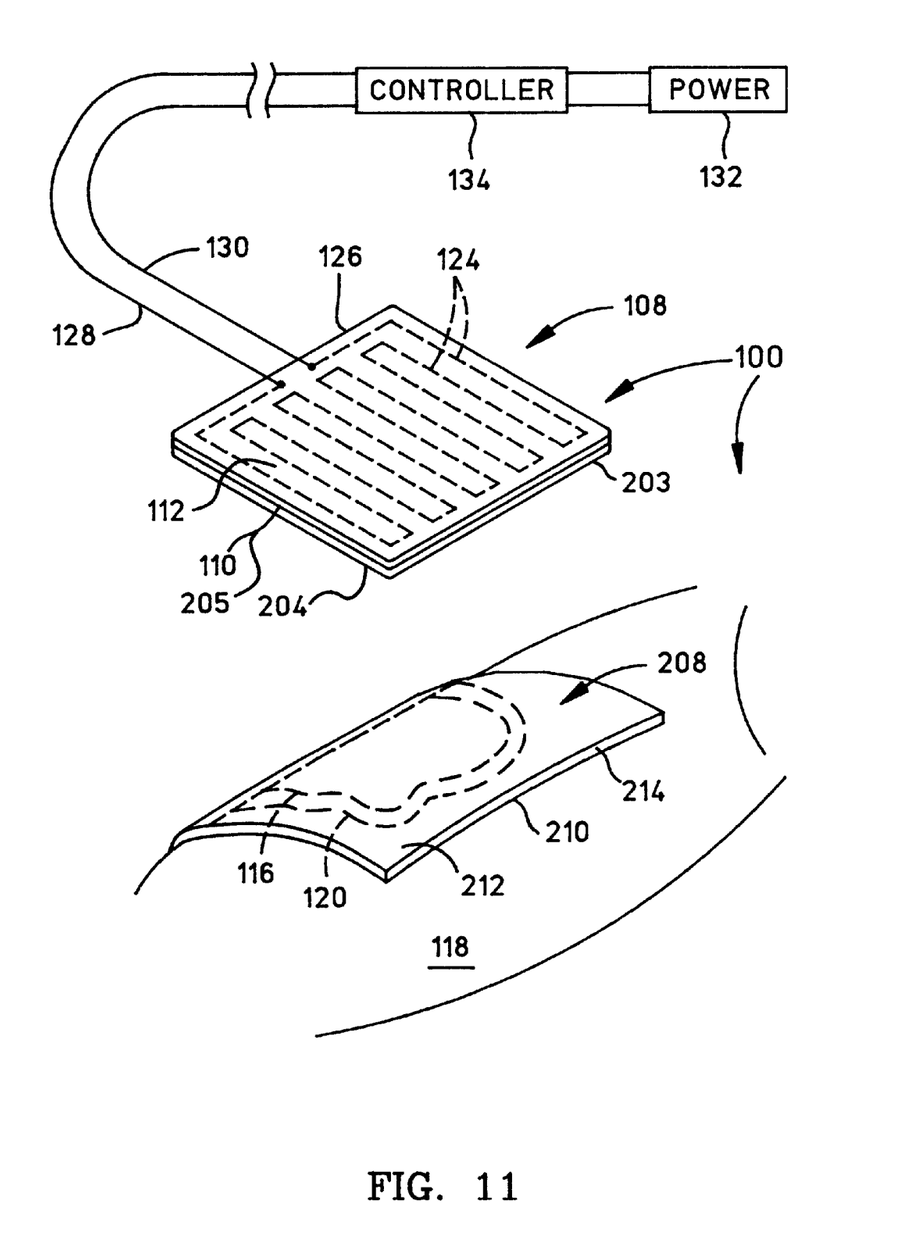
FIG. 11 illustrates an alternate embodiment of the IR bandage with bandpass filter, where the IR filter layer is attached to the heater.

FIG. 11 illustrates an alternate embodiment of the IR bandage with bandpass filter, where the IR filter layer 203 is attached to the heater 108. Specifically, the second (upper) surface 205 of IR filter layer 203 is attached to the first surface 110 of heater 108. The provision of the heater 108 and IR filter layer 203 as a single unit, to the user, simplifies the treatment regimen and purchasing process. This one-piece component can be reused in subsequent therapies, even if a new bandage 208 is required. Furthermore, the bandage layer 208 may be chosen from a plurality of alternate materials, depending on availability or therapy, without affecting the relationship between the IR filter layer 203 and the heater 108.

Figure 12:
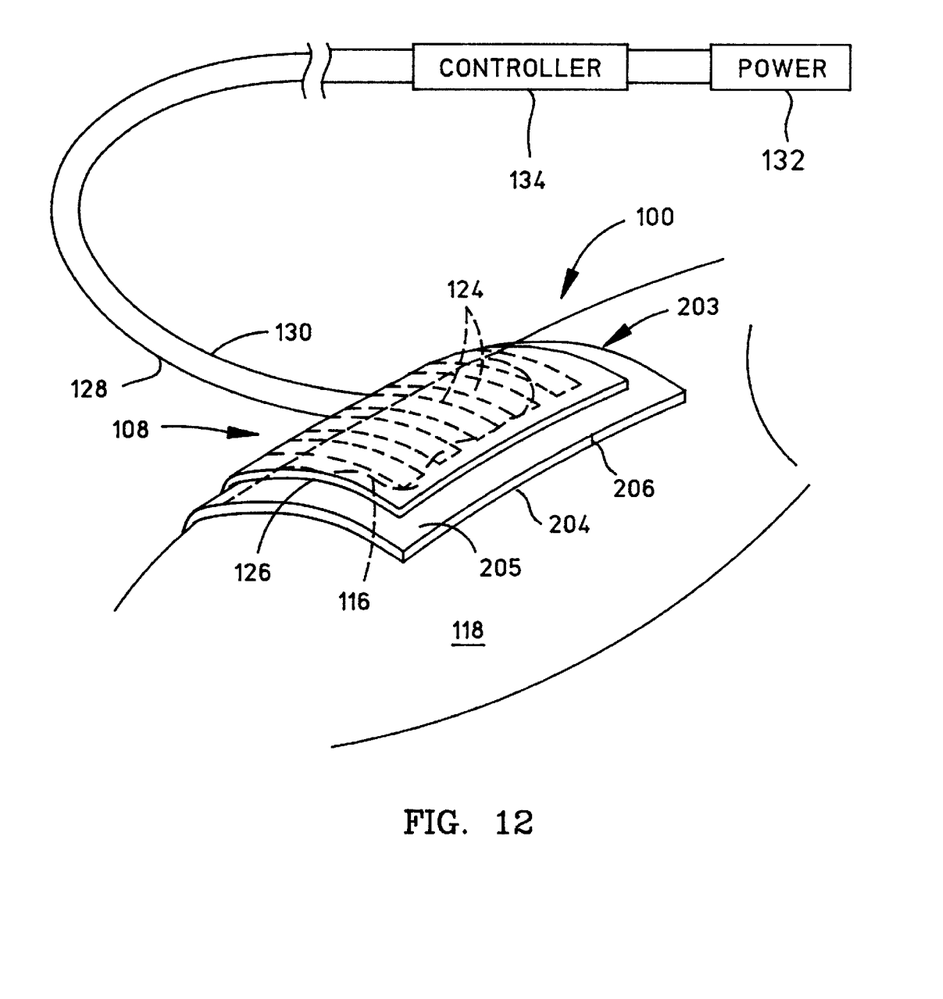
FIG. 12 illustrates an alternate embodiment of the IR bandage with bandpass filter, where the IR filter layer is attached directly to the skin, overlying the tissue treatment area.

FIG. 12 illustrates an alternate embodiment of the IR bandage with a bandpass filter, where the IR filter layer 203 is attached directly to the skin 118, overlying the tissue to be treated. In this aspect of the invention the IR filter layer 203 is attached directly body 118, overlying the tissue, without an intervening bandage member. This aspect of the invention is similar to the embodiments illustrated in FIGS. 9 and 11, except that the IR transparent bandage 208 is not used. The first surface 204 of IR filter layer 203 is attached to the skin of the body 118, and the second surface 205 is attached to the first surface 110 of heater 108. The cost and bother of attaching a separate bandage layer is avoided in the aspect of the invention, in cases where the insult or injury is in the subdermal tissues, and the application of a bandage to protect the epidermis is unnecessary.

The third component of this invention is an attachment means to hold the heater 108 in position on, or over, the bandage 200. Such means may include, for example, a pattern of adhesive that acts between the first surface 110 of the heater 108 and the second surface 205 of the IR filter layer 203. The pattern may have, for example, the shape and composition of the pattern illustrated in FIG. 5. This pattern of adhesive may be on the second surface 205 of IR filter layer 203, or on the first surface 110 of the heater 108. Alternatively, it may comprise a separate film of two-sided adhesive between the surfaces 205 and 110. Other attachment means contemplated for use in this invention include, without limitation, hook-and-eye material, a pocket formed on the second surface 205 of IR filter layer 203, tabs, tapes, straps, clamps, and so forth. The function of the attachment means is to hold the heater 108 in close proximity to the IR filter layer 203. The function may result in full or partial contact between the first surface 110 of the heater 108 and the second surface 205 of the IR filter layer 203, or may even result in the heater 108 being held slightly off of the second surface 205, out of direct contact with the IR filter layer 203.

Clearly, other embodiments and modifications of this invention will occur readily to those of ordinary skill in the art in view of these teachings. Therefore, this invention is to be limited only by the following claims, which include all such embodiments and modifications when viewed in conjunction with the above specification and accompanying drawings.

We claim:

1. A tissue treatment apparatus comprising:
    a bandage having first surface for facing tissue and a second surface;
    the bandage including an infrared (IR) filter layer which is transmissive to energy in the IR electromagnetic spectrum that passes through the bandage between the bandage first surface and the bandage second surface; and
    means for adhering the first surface of the bandage to a person's skin.

2. The apparatus of claim 1 wherein the IR filter layer has IR attenuation characteristics that are responsive to the IR wavelength.

3. The apparatus of claim 1 in which the IR filter layer has a response that attenuates a center IR wavelength at a first attenuation level, and attenuates off-center wavelengths at a second attenuation level, greater than the first attenuation level.

4. The apparatus of claim 3 in which the IR filter layer center wavelength is approximately 16 microns.

5. The apparatus of claim 3 in which the IR filter layer is transparent at the center wavelength.

6. The apparatus of claim 1 in which the IR filter layer is transparent to energy in the IR wavelengths between 3 and 30 microns.

7. The apparatus of claim 6 in which the IR filter layer is an IR bandpass filter.

8. The apparatus of claim 7, in which the IR transparent layer is a flexible, planar member fabricated of a material selected from the group consisting of polyurethane, polyethylene, polypropylene, and polyvinyl chloride.

9. The apparatus of claim 8, wherein the IR transparent layer comprises a polymeric film.

10. The apparatus of claim 9, wherein the film has a thickness of about 127 microns.

11. The apparatus of claim 9, wherein the film has a thickness of less than 127 microns.

12. The apparatus of claim 9, wherein the polymeric film is an uncoated polymeric film.

13. The apparatus of claim 1 which the bandage further includes am IR transparent layer which is transparent to energy in the IR electromagnetic spectrum.

14. The apparatus of claim 13 in which the IR transparent layer has a first surface and a second surface, in which the IR filter layer has a first surface and a second surface, in which the IR transparent layer first surface defines the bandage first surface, in which the IR filter layer first surface overlies the IR transparent layer second surface, and in which the IR filter layer second surface defines the bandage second surface.

15. The apparatus of claim 13, wherein the heater is substantially planar.

16. The apparatus of claim 15, wherein the heater is flexible.

17. The apparatus of claim 15, wherein the heater includes means for uniformly heating the heater.

18. The apparatus of claim 15, wherein the heater includes means for heating a portion of the heater.

19. The apparatus of claim 1 further comprising:

a heater to radiate energy in the IR electromagnetic spectrum;

the heater being positioned over the second surface of the bandage; and an attachment means acting between the heater and the second surface for retaining the heater over the bandage's second surface.

20. The apparatus of claim 19, wherein the heater has a first surface and the attachment means acts between the first surface of the heater and the second surface of the bandage.

21. The apparatus of claim 20, wherein a portion of the first surface of the heater contacts a portion of the second surface of the bandage.

22. The apparatus of claim 20, wherein the first surface of the heater contacts the second surface of the bandage.

23. The apparatus of claim 20, wherein the attachment means includes a pattern of adhesive acting between the first surface of the heater and the second surface of the bandage.

24. The apparatus of claim 19, wherein the attachment means includes a pattern of adhesive between the heater and the second surface of the bandage.

25. The apparatus of claim 19 wherein the heater is electrically actuated.

26. The apparatus of claim 25 wherein the heater includes a flexible planar member and an electrical resistance element embedded in the flexible planar member.

27. The apparatus of claim 1, wherein the means include a pattern of adhesive material on the first surface of the bandage.

28. The apparatus of claim 1, wherein the means include an adhesive pattern on the bandage first surface for adhering the bandage to a person.

29. The apparatus of claim 19 wherein the energy in the IR wavelengths emitted by the heater is responsive to the heater's surface temperature.

30. A tissue treatment apparatus comprising:

an infrared (IR) filter layer, having first and second surfaces, which attenuates energy in the IR electromagnetic spectrum;

a support for supporting the IR filter layer over tissue to be treated with attenuated IR energy; and means for adhering the support to a person's skin.

31. The apparatus of claim 30 wherein the support comprises:

an IR-transparent bandage having a first surface for facing tissue and a second surface underlying the IR filter layer first surface.

32. The apparatus of 30 wherein the IR filter layer is transparent to IR wavelengths in the range between 3 and 30 microns.

33. The apparatus of claim 30 further comprising:

a heater, having a first surface attached to the IR filter layer second surface, to emit energy in the IR electromagnetic spectrum.

* * * * *